United States Patent [19]

Baird et al.

[11] 4,079,050
[45] Mar. 14, 1978

[54] DISPERSE MONOAZO DYESTUFFS CONTAINING A THIOPHENE RESIDUE

[75] Inventors: David Boyd Baird; Alan Thomas Costello; Brian Ribbons Fishwick; Robert David McClelland; Peter Smith, all of Manchester, England

[73] Assignee: Imperial Chemical Industries Limited, London, England

[21] Appl. No.: 654,170

[22] Filed: Feb. 2, 1976

Related U.S. Application Data

[63] Continuation of Ser. No. 457,648, Apr. 3, 1974, abandoned, which is a continuation-in-part of Ser. No. 324,186, Jan. 16, 1973, abandoned.

[30] Foreign Application Priority Data

Jan. 28, 1972 United Kingdom ............... 4046/72
Dec. 14, 1972 United Kingdom ............. 57676/72

[51] Int. Cl.$^2$ .................. C09B 29/08; C09B 29/26
[52] U.S. Cl. .................................... 260/152; 260/156; 260/329 AM; 260/332.2 C
[58] Field of Search ............................. 260/152, 156

[56] References Cited

U.S. PATENT DOCUMENTS

| | | | |
|---|---|---|---|
| 2,683,708 | 7/1954 | Dickey et al. | 260/158 |
| 2,805,218 | 9/1957 | Towne et al. | 260/152 |
| 2,827,450 | 3/1958 | Towne et al. | 260/152 |
| 3,637,653 | 1/1972 | Von Brachel et al. | 260/152 X |
| 3,639,384 | 2/1972 | Weaver et al. | 260/152 X |
| 3,639,385 | 2/1972 | Weaver et al. | 260/152 X |
| 3,640,995 | 2/1972 | Weaver et al. | 260/152 X |

FOREIGN PATENT DOCUMENTS 2,304,218 7/1973 Germany ................ 260/152

*Primary Examiner*—Charles F. Warren
*Attorney, Agent, or Firm*—Cushman, Darby & Cushman

[57] ABSTRACT

The water-insoluble monoazo dyestuffs, free from sulphonic acid and carboxylic acid groups, which are of the formula:

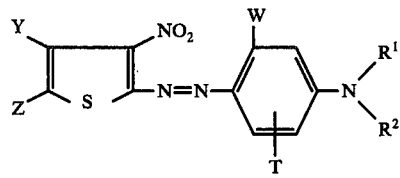

wherein Y is hydrogen, lower alkyl, optionally substituted phenyl or nitro; Z is nitro, cyano, optionally substituted phenyl, optionally substituted lower alkoxycarbonyl or carbonamido; T is hydrogen, optionally substituted lower alkyl or optionally substituted lower alkoxy;

W is an acylamino group of the formula:

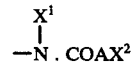

wherein $X^1$ is hydrogen or lower alkyl, $X^2$ is hydrogen or an optionally substituted hydrocarbon or heterocyclic radical, and A is a direct link or —O— or

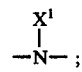

and $R^1$ and $R^2$ each independently represent a hydrogen atom or an optionally substituted alkyl radical or $R^1$ and $R^2$ together form with the nitrogen atom N a 5- or 6-membered nitrogen-containing heterocyclic ring, a process for the manufacture of the said dyestuffs by diazotization and coupling, and the use of the said dyestuffs for coloring synthetic textile materials, in particular aromatic polyester textile materials which they color in violet to green shades possessing excellent fastness to light, to wet treatments and to dry heat treatments.

3 Claims, No Drawings

DISPERSE MONOAZO DYESTUFFS CONTAINING A THIOPHENE RESIDUE

This is a continuation of application Ser. No. 457,648 filed Apr. 3, 1974, now abandoned, which is a CIP of Ser. No. 324,186 filed Jan. 16, 1973, now abandoned.

This invention relates to disperse monoazo dyestuffs which are valuable for colouring synthetic textile materials.

According to the invention there are provided the water-insoluble monoazo dyestuffs, free from sulphonic acid and carboxylic acid groups, which are of the formula:

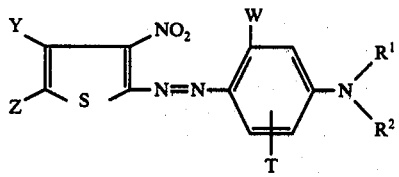

wherein Y is hydrogen, lower alkyl, optionally substituted phenyl or nitro; Z is nitro, cyano, optionally substituted phenyl, optionally substituted lower alkoxycarbonyl or carbonamido; T is hydrogen, optionally substituted lower alkyl or optionally substituted lower alkoxy;

W is an acylamino group of the formula:

wherein $X^1$ is hydrogen or lower alky, $X^2$ is hydrogen or an optionally substituted hydrocarbon or heterocyclic radical, and A is a direct bond or —O— or

and $R^1$ and $R^2$ each independently represent a hydrogen atom or an optionally substituted alkyl radical or $R^1$ and $R^2$ together form with the nitrogen atom N a 5- or 6-membered nitrogen-containing heterocyclic ring.

Throughout this specification the terms "lower alkyl" and "lower alkoxy" are used to denote alkyl and alkoxy radicals respectively containing from 1 to 4 carbon atoms.

As examples of the lower alkyl radicals represented by Y and $X^1$ there may be mentioned methyl, ethyl, n-propyl and n-butyl.

As examples of the substituted phenyl radicals represented by Y and Z there may be mentioned tolyl, chlorophenyl, nitrophenyl an nitrotolyl. As examples of the optionally substituted lower alkoxy carbonyl radicals represented by Z there may be mentioned methoxy carbonyl and ethoxycarbonyl, hydroxy lower alkoxy carbonyl such as β-hydroxyethyloxycarbonyl, cyano lower alkyl such as β-cyanoethoxycarbonyl, and lower alkoxy lower alkoxy carbonyl such as β-methoxyethoxyethoxycarbonyl. The carbonamido groups represented by Z are of the formula

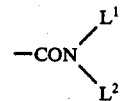

wherein $L^1$ is hydrogen, lower alkyl or phenyl, and $L^2$ is hydrogen or lower alkyl; and as examples of the said groups there may be mentioned carbonamido itself and N-methyl and N:N-diethylcarbonamido.

As examples of the optionally substituted lower alkyl radicals represented by T there may be mentioned methyl, ethyl, n-propyl and n-butyl, hydroxy lower alkyl such as βhydroxyethyl, lower alkoxy lower alkyl such as methoxymethyl, and lower alkoxycarbonyl lower alkyl such as ethoxycarbonylmethyl. As examples of the optionally substituted lower alkoxy radicals represented by T there may be mentioned methoxy and ethoxy, hydroxy lower alkoxy such as β-hydroxyethoxy, lower alkylcarbonyloxylower alkoxy such as β-acetoxyethoxy, lower alkoxy lower alkoxy such as β-methoxyethoxy and lower alkoxycarbonyl lower alkoxy such as β-methoxycarbonyl ethoxy. It is preferred that T is attached to the benzene ring in para position to W, and that T represents hydrogen, lower alkyl or lower alkoxy.

As examples of the radicals represented by $X^2$ there may be mentioned alkyl in particular lower alkyl such as methyl, ethyl, propyl and butyl, hydroxy lower alkyl such as β-hydroxyethyl, cyano lower alkyl such as β-cyanoethyl, chloro lower alkyl such as chloromethyl, lower alkylcarbonyl lower alkyl such as acetylmethyl, lower alkyl carbonyloxy lower alkyl such as β-acetoxyethyl, phenyl and substituted derivatives thereof such as tolyl, anisyl, dimethoxyphenyl and chlorophenyl, and heterocyclic radicals such as pyrid-2-yl and thien-2-yl radicals. It is however preferred that W represents an acylamino group of the formula

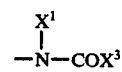

wherein $X^3$ is lower alkoxy and preferably hydrogen or lower alkyl, and $X^1$ is lower alkyl and preferably hydrogen.

The preferred dyestuffs of the invention are represented by the formula:

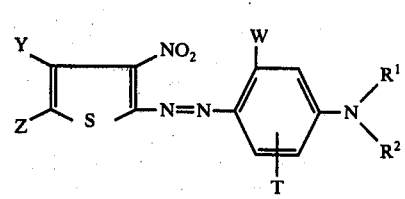

wherein Y is selected from the group consisting of hydrogen, lower alkyl, phenyl, nitrophenyl and nitro;

Z is selected from the group consisting of nitro, cyano, phenyl, nitrophenyl, nitrotolyl, lower alkoxycarbonyl, lower alkoxy lower alkoxycarbonyl and a carbonamido group of the formula:

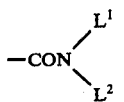

wherein L¹ is selected from the group consisting of hydrogen and lower alkyl, and L² is selected from the group consisting of hydrogen, lower alkyl and phenyl;

T is selected from the group consisting of hydrogen, lower alkyl, lower alkoxycarbonyl lower alkyl, lower alkoxy and lower alkylcarbonyloxy lower alkoxy;

W is an acylamino group of the formula:

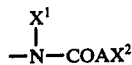

wherein S¹ is selected from the group consisting of hydrogen and lower alkyl, A is selected from a direct bond, —O— and

and X² is selected from the group consisting of hydrogen, lower alkyl,, hydroxy lower alkyl, phenyl, chlorophenyl, chloro lower alkyl, methoxyphenyl, phenoxy and lower alkoxy;

R¹ and R² are each independently selected from the group consisting of hydrogen, lower alkyl, dodecyl, cyano lower alkyl, fluoro lower alkyl, chloro lower alkyl, bromo lower alkyl, hydroxy lower alkyl, lower alkoxy lower alkyl, phenoxy lower alkyl, cyano lower alkoxy lower alkyl, lower alkoxy lower alkoxy lower alkyl, cyclohexyloxycarbonyl lower alkyl, phenoxycarbonyl lower alkyl, lower alkoxy carbonyl lower alkyl, lower alkoxy lower alkoxy carbonyl lower alkyl, benzoyl lower alkyl, allyloxycarbonyl lower alkyl, lower alkylcarbonyl lower alkyl, lower alkylcarbonyloxy lower alkyl, benzoyloxy lower alkyl, lower alkoxy lower alkyl carbonyloxy lower alkyl, lower alkyl sulphonyloxy lower alkyl, lower alkoxycarbonyl lower alkoxy lower alkyl, lower alkoxycarbonyl lower alkylthio lower alkyl, cyclohexylcarbonyloxy lower alkyl, lower alkylsulphonyl lower alkyl, lower alkoxy lower alkoxy lower alkoxycarbonyl lower alkyl, lower alkoxycarbonyl lower carbonyloxy lower alkyl, fur-2-yl lower alkyl, succinimido lower alkyl, maleimido lower alkyl, phthalimido lower alkyl, phenylthio lower alkyl, lower alkyl carbonylamino lower alkyl, lower alkoxy carbonylamino lower alkyl, phenylaminocarbonyl lower alkyl, ureido lower alkyl and N-phenyl and N-lower alkyl derivatives thereof, and benzyloxycarbonyl lower alkyl, or R¹ and R² are joined together to form with the nitrogen atom N a morpholine, piperidine, pyrrolidine or thiazine ring.

As examples of the radicals represented by R¹ and R² there may be mentioned lower alkyl radicals such as methyl, ethyl, n-propyl and n-butyl, hydroxy lower alkyl such as β-hydroxyethyl and 62 -hydroxybutyl, lower alkoxy lower alkyl such as β-ethoxyethyl and γ-methoxypropyl, cyano lower alkyl such as β-cyanoethyl chloro lower alkyl such as β-chloroethyl and γ-chloropropyl, bromo lower alkyl such as β-bromoethyl, fluoro alkyl such as β:β: β:-trifluoroethyl, lower alkylcarbonyloxy lower alkyl such as β-acetoxyethyl, lower alkoxycarbonyl lower alkyl such as β-(methoxy- or butyloxy-carbonyl) ethyl and α:β-di(methoxycarbonyl)ethyl, hydroxy lower alkoxy carbonyl lower alkyl such as β-(β'-hydroxyethoxycarbonyl)ethyl, lower alkoxy lower alkoxycarbonyl lower alkyl such as β-(β'-methoxyethoxycarbonyl)ethyl, lower alkoxy lower alkoxy lower alkoxycarbonyl lower alkyl such as β-[β'-(β''-methoxyethoxy)ethoxy carbonyl]ethyl, benzoyloxy lower alkyl such as β-benzoyloxy ethyl, lower alkoxycarbonyloxy lower alkyl such as β-ethoxycarbonyloxy ethyl, lower alkylsulphonyloxy lower alkyl such as β-methoxy- sulphonyloxyethyl, lower alkylcarbonyl lower alkyl such as β-acetylethyl, lower alkoxycarbonyloxy lower alkyl such as β-ethoxycarbonyloxy ethyl, lower alkylsulphonyloxy lower alkyl such as β-methylsulphonyloxyethyl, lower alkylcarbonyl lower alkyl such as β-acetylethyl, lower alkoxy lower alkyl carbonyloxy lower alkyl such as β-(α'-methoxypropionyl)ethyl, benzoyl lower alkyl such as benzoylmethyl, lower alkoxycarbonyl lower alkoxy lower alkyl such as β-(β'-methoxycarbonylethosy)ethyl, lower alkoxy carbonyl lower alkylthio lower alkyl such as β-(ethoxycarbonyl-methylthio)ethyl, ethyl, cyclohexyloxycarbonyl lower alkyl such as β-cyclohexyloxycarbonyl lower alkyl such as β-cyclohexyloxycarbonyl-ethyl, lower alkyl sulphonyl lower alkyl such as β-methylsulphonyl ethyl, phenoxycarbonyloxy lower alkyl such as β-phenoxycarbonyl-oxyethyl and β-anisyloxycarbonyloxyethyl, phenoxy lower alkyl such as β-phenoxy ethyl, cyano lower alkoxy lower alkyl such as β-(β-cyano-ethoxy) ethyl, lower alkoxy lower alkoxy lower alkyl such as β-(β'-methoxyethoxy) ethyl, phenoxycarbonyl lower alkyl such as β-(phenoxy- carbonyl) ethyl, benzoyl lower alkyl such as γ-benzoylpropyl, allyloxycarbonyl lower alkyl such as β-(allyloxycarbonyl)ethyl, cyclohexylcarbonyloxy lower alkyl such as β-(cyclohexylcarbonyloxy) ethyl, lower alkoxy lower alkoxy lower alkoxycarbonyl lower alkyl such as β-[β'-(β''-methoxyethoxy)ethoxycarbonyl]ethyl, lower alkoxycarbonyl lower alkoxycarbonyloxy lower alkyl such as β-[β'-(ethoxycarbonyl)ethoxycarbonyloxy]ethyl, fur-2-yl lower alkyl such as fur-2 -yl methyl, succinimido lower alkyl such as β-succinimidoethyl, maleimido lower alkyl such as γ-maleimidopropyl, phthalimido lower alkyl such as β-phthalimidoethyl, phenylthiomethyl, lower alkyl carbonylamino lower alkyl such as β-(acetylamino)ethyl, lower alkoxycarbonylamino lower alkyl such as β-(methoxycarbonyl amino) ethyl, phenylaminocarbonyl lower alkyl such as γ-(anilino-carbonyl)propyl, ureido lower alkyl such as β-ureidoethyl and N-phenyl and N-lower alkyl derivatives thereof such as β-(N-phehylureido) ethyl and γ-(N:N-diethylureido)propyl, and benzyloxycarbonyl lower alkyl such as ⊖-(benzyloxycarbonyl)ethyl.

It is however preferred that R¹ and R² together contain not more than one hydroxy group.

According to a further feature of the invention there is provided a process for the manufacture of the azo dyestuffs as hereinbefore defined which comprises diazotizing amine of the formula:

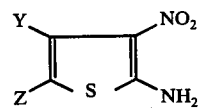   Formula I and coupling the resulting diazo compound with a coupling component of the formula:

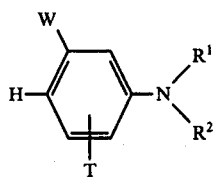

wherein Y, Z, W, T, $R^1$ and $R^2$ have the meanings stated, the amine and coupling component being free from carboxylic acid and sulphonic acid groups.

The process of the invention can be conveniently carried out by adding sodium nitrite to a solution or dispersion of the amine in a strong inorganic acid or an aqueous solution thereof, or preferably by stirring the amine with nitrosylsulphuric acid, and adding the resulting solution or dispersion of the diazo component to a solution of the coupling component in water or in a mixture of water and a water-miscible organic liquid, if necessary adjusting the pH of the mixture to facilitate the coupling reaction, and finally isolating the resulting dyestuff by conventional methods.

The amines of Formula I can themselves be obtained by the conventional methods used for the production of thiophene derivatives. Thus, for example, a 2-halogenothiophene can be nitrated and the halogen atom in the 2-position is then converted to an amino group by treatment with ammonia. Alternatively 2-aminothiophenes containing electron withdrawing groups can be prepared by conventional methods from compounds obtained by the methods described in Chemische Berichte, Volume 98 at page 3571 (1965) and Volume 99 at page 94 (1966).

As specific examples of amines of Formula I there may be mentioned, for example, 2-amino-3:5-dinitrothiophene, 2-amino-3:4:5-trinitrothiophene, and 2-amino-3-nitro-5-(carbonamido, cyano or methoxy carbonyl) thiophene. The preferred amine is 2-amino-3:5-dinitrothiophene.

As specific examples of said coupling components there may be mentioned N:N-diethyl-m-aminoacetanilide, N:N-di($\beta$-acetoxyethyl)-m-aminoacetanilide, 2-methoxy-5-(formylamino- or acetylamino)-N-[$\beta$-($\beta'$-methoxyethoxycarbonyl)ethyl]aniline, m-N:N-diethylamino-$\beta$-chloropropionanilide and m-N:N-di-n-butyl-formanilide.

A preferred class of the dyestuffs of the invention comprises the dyestuffs wherein Y is hydrogen and Z is nitro.

A second preferred class of the dyestuffs of the invention comprises the dyestuffs of the formula:

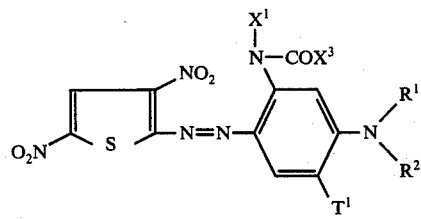

wherein $R^1$ and $R^2$ have the meanings stated, $T^1$ is hydrogen, lower alkyl or lower alkoxy, $X^1$ is lower alkyl and preferably hydrogen, and $X^3$ is hydrogen and preferably lower alkyl.

The azo dyestuffs of the invention are valuable for coloring synthetic textile materials in particular secondary cellulose acetate and cellulose triacetate textile materials, polyamide textile materials such as polyhexamethylene adipamide textile materials, and, above all, aromatic polyester textile materials such as polyethylene terephthalate textile materials. Such materials can be in the form of filaments, fibres or woven or knitted materials.

The said azo dyestuffs can be applied to the synthetic textile materials by methods which are conventionally employed in applying disperse dyestuffs to such textile materials. Thus the dyestuffs in the form of aqueous dispersions can be applied by dyeing, padding or printing processes using the conditions and other additives which are conventionally used in carrying out such processes. Alternatively the said dyestuffs can be applied to synthetic textile materials by solvent methods of dyeing, for example by applying a solution or dispersion of the dyestuff in perchloroethylene optionally containing a minor amount of water to the textile material preferably at elevated temperature. The dyestuffs may also be used to color synthetic polymers by melt coloration, for example using late injection techniques, followed by melt spinning of the colored polymers into fibres or filaments. Alternatively the dyestuffs can be applied to synthetic textile materials by the process of transfer color printing.

When applied to synthetic textile materials the azo dyestuffs of the invention give violet to green coloration which have excellent fastness to light and to wet and to dry heat treatments both before and after heat setting. The said dyestuffs also have high tinctorial strength, exhaust well event at a high liquor: goods ratio and have excellent dyeing, levelling, temperature range and build up properties on synthetic textile materials, particularly aromatic polyester textile materials, thus enabling heavy depths of shade to be readily obtained. In addition variations in the pH of the dyebaths have little effect on the shades of the resulting dyeings.

The invention is illustrated but not limited by the following Examples in which the parts and percentages are by weight:

EXAMPLE 1

7.6 Parts of sodium nitrite are added to 90 parts of sulphuric acid, the temperature being allowed to rise to 30° C. The mixture is then cooled to 5° C and a mixture of 50 parts of propionic acid and 300 parts of acetic acid added, the temperature of the mixture being allowed to rise to 15° C and then maintained at this temperature. The mixture is then cooled to 0° C, 18.9 parts of 2-amino-3:5-dinitrothiophene are added over 30 minutes and the mixture is stirred for 20 minutes at 0° C. The resulting solution is added to a solution of 31 parts of 2-methoxy-5-acetylamino-N-$\beta$-[$\beta'$-(methoxyethoxycarbonyl)ethyl]aniline in 300 parts of water containing 30 parts of a concentrated aqueous solution of hydrochloric acid and 350 parts of ice. The mixture is stirred for 50 minutes at 0° C and the precipitated dyestuff is then filtered off, washed with water and dried.

When applied to aromatic polyester textile materials from an aqueous dispersion the dyestuff yields green shades of excellent fastness properties.

The 2-amino-3:5-dinitrothiophene was itself obtained by reacting the sodium salt of cyanoacetic acid with the dimer of mercaptoacetaldehyde in aqueous medium at 80° C, cooling to 20° C, adding acetic anhydride while maintaining the pH at 6–7, acidifying and isolating the 2-acetylaminothiophene-3-carboxylic acid. This was then dinitrated in sulphuric acid medium at 0° C, the resulting 2-acetylamino-3:5-dinitrothiophene being isolated and then deacetylated by heating in an aqueous solution of sulphuric acid. Table I gives further Examples of the dyestuffs of the invention of the formula

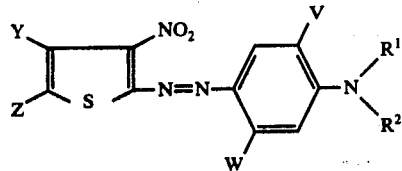

the symbols of which have the values given in the respective columns of the Table, while the last column of the Table gives the shades obtained when the dyestuffs are applied to an aromatic polyester textile material.

The dyestuffs of these Examples were obtained by diazatizing the appropriate amine of the formula:

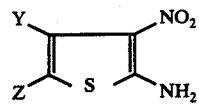

and coupling the resulting diazo compound with the appropriate coupling component of the formula

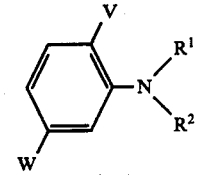

using methods similar to that described in Example 1.

TABLE I

| Example | Y | Z | V | W | R¹ | R² | Shade |
|---|---|---|---|---|---|---|---|
| 2 | H | nitro | H | acetylamino | ethyl | ethyl | Bluish-Green |
| 3 | methyl | " | " | " | β-acetoxyethyl | β-acetoxyethyl | " |
| 4 | nitro | " | methoxy | " | H | β-(β'-methoxyethoxycarbonyl)ethyl | Green |
| 5 | H | methoxycarbonyl | H | " | ethyl | ethyl | Greenish-blue |
| 6 | " | N:N-diethylcarbonamido | " | " | " | " | " |
| 7 | " | cyano | " | " | " | " | " |
| 8 | " | nitro | methoxy | " | " | " | Green |
| 9 | " | " | " | " | H | β-methoxyethyl | " |
| 10 | " | " | H | " | β-(β'-methoxyethoxycarbonyl)ethyl | β-(β'-methoxyethoxycarbonyl)ethyl | Greenish-blue |
| 11 | " | " | " | " | H | " | " |
| 12 | " | " | " | " | β-methoxyethyl | β-methoxyethyl | Bluish-green |
| 13 | " | " | methoxy | " | β-(β'-methoxyethoxycarbonyl)ethyl | ethyl | Green |
| 14 | " | " | H | chloracetylamino | ethyl | ethyl | Bluish-Green |
| 15 | " | " | " | acetylamino | β-cyanoethyl | β-(β'-methoxyethoxycarbonyl)ethyl | Greenish-blue |
| 16 | " | " | " | " | " | H | " |
| 17 | " | " | " | " | β-hydroxyethyl | β-hydroxyethyl | Bluish-green |
| 18 | " | " | " | " | β-acetoxyethyl | β-acetoxyethyl | Greenish-blue |
| 19 | " | " | " | " | β-chloroacetoxyethyl | β-chloroacetoxyethyl | " |
| 20 | " | " | " | " | β-hydroxypropyl | β-hydroxypropyl | Bluish-green |
| 21 | " | " | " | " | β-acetoxypropyl | β-acetoxypropyl | Greenish-blue |
| 22 | " | " | " | α-acetylacetylamino | H | H | " |
| 23 | " | " | " | phenoxycarbonylamino | β-acetoxyethyl | β-acetoxyethyl | " |
| 24 | " | " | " | formylamino | n-butyl | n-butyl | Bluish-green |
| 25 | " | " | " | " | β-benzoyloxyethyl | β-benzoyloxyethyl | Greenish-blue |
| 26 | " | " | methoxy | 3:4-dimethoxybenzoylamino | β-methoxycarbonylethyl | β-methoxycarbonylethyl | Green |
| 27 | " | " | ethoxy | acetylamino | β-ethoxycarbonyloxyethyl | β-ethoxycarbonyloxyethyl | " |
| 28 | " | " | H | acetylamino | γ-hydroxypropyl | γ-hydroxypropyl | Bluish-green |
| 29 | " | " | " | " | ethyl | n-dodecyl | " |
| 30 | " | " | " | " | ethyl | ω-hydroxypentyl | " |
| 31 | " | " | methoxy | N-methylacetylamino | β-acetoxyethyl | β-acetoxyethyl | Green |
| 32 | " | " | " | formylamino | β-(cyanoacetoxy)ethyl | β-(cyanoacetoxy)ethyl | " |
| 33 | " | " | " | β-acetoxypropionylamino | β-acetoxyethyl | β-acetoxyethyl | " |
| 34 | " | " | " | methoxycarbonylamino | β-(allyloxycarbonyl)ethyl | β-(allyloxycarbonyl)ethyl | " |
| 35 | " | " | H | acetylamino | β-methylsulphonyloxyethyl | β-methylsulphonyloxyethyl | Greenish-blue |
| 36 | " | " | " | " | ethyl | β-succinimidoethyl | Bluish-green |
| 37 | " | " | " | ureido | H | H | Greenish-blue |
| 38 | " | " | methoxy | " | β-acetoxyethyl | β-acetoxyethyl | Green |
| 39 | " | " | " | " | β-acetylethyl | β-acetylethyl | " |
| 40 | " | " | " | acetylamino | H | H | Greenish-blue |
| 41 | " | " | " | " | methyl | β-cyanoethyl | " |
| 42 | " | " | " | thien-2-yl carbonylamino | ethyl | ethyl | Bluish-green |
| 43 | " | " | " | ethylureido | β-acetoxyethyl | β-acetoxyethyl | " |
| 44 | " | " | H | N:N-diethylureido | β-acetoxyethyl | β-acetoxyethyl | " |
| 45 | " | " | " | β-hydroxypropyl | ethyl | ethyl | " |

TABLE I-continued

| Example | Y | Z | V | W | R¹ | R² | Shade |
|---|---|---|---|---|---|---|---|
| 46 | " | " | " | ionylamino " | β-chloroethyl | β-chloroethyl | Greenish-blue |
| 47 | " | " | " | acetylamino | β-(β'-methoxy-propionyl)ethyl | ethyl | Bluish-green |
| 48 | " | " | " | " | β:γ-dihydroxypropyl | " | " |
| 49 | " | " | " | " | α:β-di(ethoxy-carbonyl)ethyl | " | " |
| 50 | " | " | " | " | β-(β'-cyano ethoxy)ethyl | " | " |
| 51 | " | " | " | " | methyl | β-(β'-methoxycar-bonylethoxy)ethyl | " |
| 52 | " | " | " | " | ethyl | β-(ethoxycarbonyl-methylthio)ethyl | " |
| 53 | " | " | ethoxy carbonylmethyl | " | " | ethyl | " |
| 54 | " | " | methyl | " | H | β-hydroxyethyl | Green |
| 55 | " | " | β-acetoxy-ethoxy | " | β-acetoxyethyl | β-acetoxyethyl | Bluish-green |
| 56 | " | " | H | " | β-(cyclohexyl-carbonyloxy)ethyl | H | Greenish-blue |
| 57 | " | " | " | " | ethyl | benzoylmethyl | " |
| 58 | " | " | " | " | β-(cyclohexyloxy-carbonyl)ethyl | β-(cyclohexyloxy-carbonyl)ethyl | " |
| 59 | " | " | " | " | ethyl | β-(p-anisyloxy-carbonyloxy)ethyl | Bluish-green |
| 60 | " | " | " | " | ethyl | β-(diethylamino-carbonyloxy)ethyl | " |
| 61 | " | " | " | " | " | β-(m-toluidino-carbonyl)ethyl | " |
| 62 | " | " | " | " | " | β-(ethylsulphonyl)ethyl | Greenish-blue |
| 63 | " | " | " | " | " | β-(bromoacetyl-amino)ethyl | Bluish-green |
| 64 | methyl | " | " | " | β-hydroxyethyl | β-hydroxyethyl | Greenish-blue |
| 65 | " | " | " | " | ethyl | ethyl | " |
| 66 | " | " | methoxy | " | n-butyl | β-(β'-methoxyeth-oxycarbonyl)ethyl | " |
| 67 | " | " | H | " | β-cyanoethyl | β-(β'-methoxyeth-oxycarbonyl)ethyl | Blue |
| 68 | H | " | methoxy | " | H | β-[β'-(β"-methoxy-ethoxy)ethoxycar-bonyl ethyl] | Green |
| 69 | " | methoxy carbonyl | " | " | " | β-(β'-methoxyeth-oxycarbonyl)ethyl | Blue |
| 70 | " | ethoxy carbonyl | H | " | β-methoxycarbonyl ethyl | β-methoxycarbonyl-ethyl | " |
| 71 | " | β-methoxy-ethoxy-carbonyl | " | " | ethyl | ethyl | " |
| 72 | " | nitro | " | " | β-(β'-ethoxy-carbonylpropionyl-oxy)ethyl | β-(β'-ethoxycarbon-ylpropionyloxy)-ethyl | Greenish-blue |
| 73 | " | carbonamido | " | " | β-acetoxyethyl | β-acetoxyethyl | Blue |
| 74 | " | N-phenyl carbonamido | " | " | β-hydroxyethyl | β-hydroxyethyl | " |
| 75 | " | cyano | " | " | β-acetoxyethyl | β-acetoxyethyl | Greenish-blue |
| 76 | " | " | " | methoxy | H | β-(β'-methoxyeth-oxycarbonyl)ethyl | Bluish-green |
| 77 | " | " | ethoxy | " | ethyl | β-(β'-methoxyeth-oxycarbonyl)ethyl | " |
| 78 | " | " | H | ethoxycarbonyl-amino | β-acetoxyethyl | β-acetoxyethyl | Greenish-blue |
| 79 | " | " | " | acetylamino | β-cyanoethyl | β-(β'-methoxyeth-oxycarbonyl)ethyl | " |
| 80 | " | " | " | " | H | ethyl | " |
| 81 | methyl | " | " | " | ethyl | " | " |
| 82 | p-nitro phenyl | nitro | " | " | β-hydroxyethyl | β-hydroxyethyl | Green |
| 83 | H | 2-nitro-4-methylphenyl | " | " | ethyl | ethyl | Blue |
| 84 | " | cyano | " | " | β-hydroxyethyl | β-hydroxyethyl | " |
| 85 | " | " | " | " | β-methoxyethyl | β-methoxyethyl | Greenish-blue |
| 86 | " | " | " | " | β-acetylethyl | ethyl | " |
| 87 | " | " | " | " | β-propionyloxyethyl | β-propionyloxyethyl | " |
| 88 | " | " | " | ureido | ethyl | ethyl | " |
| 89 | " | " | " | benzoylamino | β-hydroxyethyl | β-hydroxyethyl | " |
| 90 | " | nitro | " | acetylamino | β-phenoxyethyl | β-phenoxyethyl | Bluish-green |
| 91 | " | " | " | propionylamino | H | β-(p-chlorophen-oxy)ethyl | Green |
| 92 | " | " | " | acetylamino | β-(cyclohexyl-oxycarbonyl)ethyl | β:β-dimethylethyl | Bluish-green |
| 93 | methyl | " | " | " | β-(n-amyloxy-carbonyl)ethyl | β-(n-amyloxycarb-onyl)ethyl | Greenish-blue |
| 94 | H | " | " | " | β-(n-butylcarb-onyloxy)ethyl | β-(n-butylcarbonyl-oxy)ethyl | " |
| 95 | " | " | " | " | ethyl | β-methyl-β-(meth-oxycarbonyl)ethyl | Bluish-green |
| 96 | " | " | " | " | " | β-methyl-β-(N-ethylcarbamoyl)ethyl | " |
| 97 | " | " | " | " | " | β-carbamoylethyl | " |
| 98 | " | " | " | " | α-methyl-β-(ethoxy | α-methyl-β-(ethoxy | Greenish-blue |

TABLE I-continued

| Example | Y | Z | V | W | R¹ | R² | Shade |
|---|---|---|---|---|---|---|---|
|  |  |  |  |  | carbonyl)ethyl | carbonyl)ethyl |  |
| 99 | " | " | " | " | H | fur-2-yl methyl | Green |
| 100 | " | " | " | " | β-(β'-methoxyethoxy)ethyl | β-(β'-methoxyethoxy)ethyl | Bluish-green |
| 101 | methyl | ethoxycarbonyl | " | " | ethyl | β-acetoxyethyl | Blue |
| 102 | " | " | " | " | " | γ-chloro-β-hydroxypropyl | " |
| 103 | H | " | methoxy | " | H | β:β:β-trifluoroethyl | " |
| 104 | " | nitro | H | acetylamino | ethyl | β-bromoethyl | Bluish-green |
| 105 | " | " | " | " | β-(cyclohexyloxycarbonyl)ethyl | β-cyanoethyl | Greenish-blue |
| 106 | " | " | " | " | ethyl | β-(maleimido)ethyl | Bluish-green |
| 107 | " | " | " | ethoxycarbonylamino | " | β-(phthalimido)ethyl | " |
| 108 | " | " | " | acetylamino | β:β-dimethylethyl | β-(phenylthio)ethyl | " |
| 109 | " | " | H | formylamino | ethyl | β-(p-tolylcarbonyl)ethyl | Greenish-blue |
| 110 | " | " | " | acetylamino | " | β-(phenylureido)ethyl | " |
| 111 | " | " | " | " | " | β-(ethylureido)ethyl | " |
| 112 | " | " | ethoxy | " | H | β-(m-chloroanilinocarbonyl)ethyl | Green |
| 113 | " | " | H | " | methyl | β-(acetylamino)ethyl | Bluish-green |
| 114 | " | " | " | " | ethyl | β-(ethoxycarbonylamino)ethyl | " |
| 115 | " | " | " | " | ethyl | β-(acetylacetyloxy)ethyl | " |
| 116 | " | " | " | " | β:β-dimethylethyl | β-(ethoxycarbonyl)ethyl | " |
| 117 | " | " | " | " | β-(cyclohexyloxy-xy-carbonyl)ethyl | β-(cyclohexyloxycarbonyl)ethyl | Greenish-blue |
| 118 | " | " | " | m-chlorobenzoylamino | ethyl | β-(β'-hydroxycarbonyl)ethyl | Bluish-green |
| 119 | " | " | " | acetylamino | " | β-(benzyloxycarbonyl)ethyl | " |
| 120 | " | " | " | " | β-(methoxycarbonyl)ethyl | β-(methoxycarbonyl)ethyl | Greenish-blue |
| 121 | " | " | methoxy | " | β-(methoxycarbonyl)ethyl | β-(methoxycarbonyl)ethyl | Green |
| 122 | " | " | " | " | ethyl | β-(vinylsulphonyl)ethyl | Greenish-blue |
| 123 | " | " | " | " | " | β-(p-chlorobenzenesulphonyl) ethyl | " |

Table II gives further Examples of the dyestuffs of the invention which are obtained by diazotizing 2-amino-3:5-dinitrothiophene and coupling the resulting diazo compound with the coupling components listed in the second column of the table using methods similar to that described in Example 1. The shades obtained on aromatic polyester textile materials from the resulting dyestuffs are given in the last column of the table.

TABLE II

| Ex. | Coupling Component | Shade |
|---|---|---|
| 124 | N-(3-acetylaminophenyl)pyrrolidine | Bluish-green |
| 125 | N-(3-acetylaminophenyl)morpholine | " |
| 126 | 1:4-dioxo-4-(m-acetylaminophenyl)-1:4 thiazine | " |
| 127 | 2-methyl-3-acetylaminoaniline | " |

The 2-amino-3:5-dinitro-4-methylthiophene used in the above examples was itself obtained as follows:

Chloracetone was reacted with sodium hydrosulphide in h aqueous medium, and the resulting solution was treated with ethylcyanoacetate in the presence of triethylamine at the boil. Addition of water precipitated 2-amino-3-ethoxycarbonyl-4-methylthiophene which was acetylated and then heated with an aqueous solution of sodium hydroxide to give 2-acetylamino-4-methylthiophene-3-carboxylic acid. This was decarboxylated by heating in N:N-diethylaniline at 220° C, the product dinitrated in sulphuric acid medium at −5° C, and then deacetylated by heating in an aqueous solution of sulphuric acid.

The 2-amino-3:4:5-trinitrothiophene was obtained by reacting 2-bromo-3:4:5-trinitrothiophene (Journal of Organic Chemistry 1957 at page 1588) with ammonia in tetrahydrofuran.

The 2-amino-3-nitro-5-(N:N-diethylcarbamoyl)thiophene was obtained by reacting 2-bromo-3-nitrothiophene-5-carboxylic acid (Chemical Abstracts 1963 at page 3860h) with thionyl chloride in toluene in the presence of dimethylformamide, and subsequently reacting with diethylamine followed by treatment with ammonia to replace the bromine atom by amino group. The 2-amino-3-nitro-5-carbamoylthiophene and 2-amino-3-nitro-5-(N-phenylcarbamoyl)thiophene were prepared in an analogous manner, the diethylamine being replaced by ammonia and by aniline.

The 2-amino-3-nitro-5-methoxycarbonylthiophene was prepared by esterifying 2-bromo-3-nitrothiophene-5-carboxylic acid using a 9% solution of sulphuric acid in methanol and subjecting the bromoester to reaction with a concentrated aqueous solution of ammonia in the presence of dimethylformamide. The 2-amino-3-nitro-5-ethoxycarbonylthiophene was prepared in an analogous manner. The 2-amino-3-nitro-5-(β-methoxyethoxycarbonyl)thiophene was prepared by transesterification of 2-amino-3-nitro-5-methoxycarbonyl thiophene by heating it in β-methoxy ethanol in the presence of tetrabutyltitanate.

The 2-amino-3-nitro-5-cyanothiophene was prepared by converting the oxime of 2-acetylamino-5-formylthiophene (Journal of the Chemical Society 1955 at page 1701) to the 5-cyano compound by heating it with acetic anhydride, nitrating in a mixture of acetic acid and

We claim:
1. A water-insoluble monoazo dyestuff, free from carboxylic acid group and sulphonic acid group, having the formula

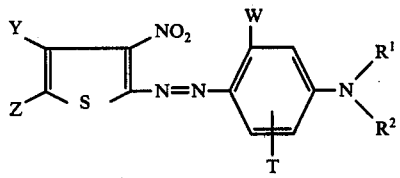

wherein Y is selected from the group consisting of hydrogen, lower alkyl, phenyl, nitrophenyl and nitro;
Z is selected from the group consisting of nitro, cyano, phenyl, nitrophenyl, nitrotolyl, lower alkoxycarbonyl, lower alkoxy lower alkoxycarbonyl and

wherein $L^1$ is selected from the group consisting of hydrogen and lower alkyl and $L^2$ is selected from the group consisting of hydrogen, lower alkyl an phenyl;
T is selected from the group consisting of hydrogen, lower alkyl alkoxycarbonyl lower alkyl, lower alkoxy and lower alkoxy;
W is

$COAX^2$ wherein $X^1$ is selected from the group consisting of hydrogen and lower alkyl, A is selected from a direct bond, —O— and

and $X^2$ is selected from the group consisting of hydrogen, lower alkyl, hydroxyl lower alkyl, phenyl, chlorophenyl, chloro lower alkyl, methoxyphenyl, phenoxy and lower alkoxy;
$R^1$ and $R^2$ are each independently selected from the group consisting of hydrogen, lower alkyl, dodecyl, cyano lower alkyl, fluoro lower alkyl, chloro lower alkyl, bromo lower alkyl, hydroxy lower alkyl, lower alkoxy lower alkyl, phenoxy lower alkyl, cyano lower alkoxy lower alkyl, lower alkoxy lower alkoxy lower alkyl, cyclohexyloxy carbonyl lower alkyl, phenoxycarbonyl lower alkyl, lower alkoxy carbonyl lower alkyl, lower alkoxy lower alkoxy carbonyl lower alkyl, benzoyl lower alkyl, allyloxycarbonyl lower alkyl, lower akylcarbonyl lower alkyl, lower alkylcarbonyloxy lower alkyl, benzoyloxy lower alkyl, lower alkoxy lower alkyl carbonyloxy lower alkyl, lower alkyl sulphonyloxy lower alkyl, lower alkoxycarbonyl lower alkoxy lower alkyl, lower alkoxycarbonyl lower alkylthio lower alkyl, cyclohexylcarbonyloxy lower alkyl, lower alkylsulphonyl lower alkyl, lower alkoxy lower alkoxy lower alkoxy carbonyl lower alkyl, lower alkoxy carbonyl lower alkylcarbonyloxy lower alkyl, fur-2-yl lower alkyl, succinimido lower alkyl, maleimido lower alkyl, phthalimido lower alkyl, phenylthio lower alkyl, lower alkyl, lower alkoxycarbonylamino lower alkyl, phenylaminocarbonyl lower alkyl, ureido lower alkyl and N-phenyl and N-lower alkyl derivatives thereof, and benzyloxy carbonyl lower alkyl, or $R^1$ and $R^2$ are joined together to form with the nitrogen atom N morpholine, piperidine, pyrrolidine or thiazine.
2. The dyestuff of claim 1 wherein Y is hydrogen and Z is nitro.
3. The dyestuff of claim 1 having the formula:

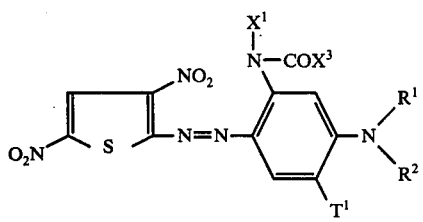

wherein $T^1$ is selected from the group consisting of hydrogen, lower alkyl and the lower alkoxy;
$X^1$ is selected from the group consisting of hydrogen and lower alkyl;
$X^3$ is selected from the group consisting of hydrogen and lower alkyl; and
$R^1$ and $R^2$ are each independently selected from the group consisting of hydrogen, lower alkyl, dodecyl, cyano lower alkyl, fluoro lower alkyl, chloro lower alkyl, bromo lower alkyl, hydroxy lower alkyl, lower alkoxy lower alkyl, phenoxy lower alkyl, cyano lower alkoxy lower alkyl, lower alkoxy lower alkoxy lower alkyl, cyclohexyloxycarbonyl lower alkyl, phenoxycarbonyl lower alkyl, lower alkoxy carbonyl lower alkyl, lower alkoxy lower alkoxy carbonyl lower alkyl, benzoyl lower alkyl, allyloxycarbonyl lower alkyl, lower alkylcarbonyl lower alkyl, lower alkylcarbonyloxy lower alkyl, benzoyloxy lower alkyl, lower alkoxy lower alkyl carbonyloxy lower alkyl, lower alkyl sulphonyloxy lower alkyl, lower alkoxycarbonyl lower alkoxy lower alkyl, lower alkoxycarbonyl lower alkylthio lower alkyl, cyclohexylcarbonyloxy lower alkyl, lower alkylsulphonyl lower alkyl, lower alkoxy lower alkoxy lower alkoxy carbonyl lower alkyl, lower alkoxy carbonyl lower alkylcarbonyloxy lower alkyl, fur-2-yl lower alkyl, succinimido lower alkyl, maleimido lower alkyl, phthalmido lower alkyl, phenylthio lower alkyl, lower alkyl carbonylamino lower alkyl, lower alkoxycarbonylamino lower alkyl, phenylamino carbonyl lower alkyl, ureido lower alkyl and N-phenyl and N-lower alkyl derivatives thereof, and benzyloxy carbonyl lower alkyl, or $R^1$ and $R^2$ are joined together to form with the nitrogen atom N morpholine, piperidine, pyrrolidine or thiazine.

* * * * *